United States Patent
Glinskii

Patent Number: 5,629,412
Date of Patent: May 13, 1997

[54] SYNTHETIC GLYCOAMINES THAT PROMOTE OR INHIBIT CELL ADHESION

[76] Inventor: Guennadi V. Glinskii, 1315 English Dr., Columbus, Mo. 65203

[21] Appl. No.: 273,506

[22] Filed: Jul. 11, 1994

[51] Int. Cl.[6] .............. A61K 38/14; C07K 9/00; C07H 13/02
[52] U.S. Cl. .............. 536/22.1; 536/115; 536/119; 530/322
[58] Field of Search .................. 514/42, 53, 54, 514/56, 62; 536/22.1, 18.7, 115, 119, 123.1, 123.13; 530/322

[56] References Cited

U.S. PATENT DOCUMENTS

| | | | |
|---|---|---|---|
| 5,081,031 | 1/1992 | Tsilibary et al. | 530/327 |
| 5,262,403 | 11/1993 | Nicolson et al. | 514/54 |

OTHER PUBLICATIONS

Chemical Abstracts, vol. 112, No. 15, issued 09 Apr. 1990, Chen et al, "Metal Complexes of Biologically Important Ligands", p. 788, col. 1, abstract No. 139749a, Z. Naturforsch., B: Chem. Sci. 1989, 44(4), pp. 459–464.

Chemical Abstracts, vol. 93, No. 7, issued 18 Aug. 1980, Mester et al, "Effect of the Interaction . . . of Poly(1–lysines)", p. 1028, col. 2, abstract No. 72242y, J. Carbohydr., Nucleosides, Nucleotides 1979, 6(2), pp. 149–166 (Eng).

(List continued on next page.)

*Primary Examiner*—John Kight
*Assistant Examiner*—Everett White
*Attorney, Agent, or Firm*—McCutchen, Doyle, Brown & Enersen

[57] ABSTRACT

A class of molecules that alter cell adhesion. A cell adhesion affector according to the present invention essentially consists of an amino acid linked to a carbohydrate wherein the amino acid and the carbohydrate are linked to form a compound chosen from the group consisting of Schiff bases, N-glycosides, esters, and Amadori products. The carbohydrate is preferably a monosaccharide or a small oligosaccharide. The carbohydrate and amino acid sub-units may be chemically modified. For example, the amino acid may be modified by covalently bonding other groups to the amino group, carboxyl group, or side chain group of the amino acid. The carbohydrate sub-unit is preferably a pentose such as arabinose, xylose, ribose, ribulose, a hexose such as fructose, deoxyfructose, galactose, glucose, mannose, tagatose, rhamnose, or a disaccharade based on two of the above such as maltose, lactose, maltulose, or lactulose.

8 Claims, 1 Drawing Sheet

OTHER PUBLICATIONS

Nathan Sharon and Halina Lis, "*Carbohydrates in Cell Recognition*", Scientific American, pp. 82–89 Jan. 1993.

Masatoshi Takeichi, "*Cadherin Cell Adhesion Receptors as a Morphogenetic Regulator*", Science, vol. 251, pp. 1451–1455, Mar. 22, 1991.

Richard O. Hynes, "*Integrins: Versatility, Modulation, and Signaling in Cell Adhesion*", Review, Cell, vol. 69, pp. 11–25, Apr. 3, 1992.

Eugene C. Butcher, "*Leukocyte–Endothelial Cell Recognition: Three (or More) Steps to Specificity and Diversity*", Minireview, Cell, vol. 67, pp. 1033–1036, Dec. 20, 1991.

Timothy A. Springer and Laurence A. Lasky, "*Sticky Sugars for Selectins*", Nature, vol. 349, pp. 196–197 Jan. 17, 1991.

Sen–itiroh Hakomori, "*Possible Functions of Tumor–Associated Carbohydrate Antigens*", The Biomembrane Institute and University of Washington, Seattle, Washington, USA, pp. 646–653, Current Opinion in Immunology 1991, 3:646–653.

Yukihide Iwamoto, Frank A. Robey, Jeannette Graf, Makoto Sasaki, Hynda K. Kleinman, Yoshikhiko Yamada, George R. Martin, "*YIGSR, a Synthetic Laminin Pentapeptide, Inhibits Experimental Metastasis Formation*", Science, vol. 238, pp. 1132–1134, issued 20 Nov. 1987.

Martin J. Humphries, Kenneth Olden, Kenneth M. Yamada, "*A Synthetic Peptide from Fibronectin Inhibits Experimental Metastasis of Murine Melanoma Cells*", Science, vol. 233, pp. 467–470, Jul. 25, 1986.

Ikuo Saiki, Junya Yoneda, Yu Igarashi, Miho Aoki, Naoto Kusunose, Kei–ichi Ono and Ichiro Azuma, "*Antimetastatic Activity of Polymeric RGDT Peptides Conjugated with Poly-(ethylene glycol)*", Jpn. J. Cancer Res., 84, pp. 558–565, May 1993.

Masayuki Miyake and Sen–itiroh Hakomori, "*A Specific Cell Surface Glycoconjugate Controlling Cell Motility: Evidence by Functional Monoclonal Antibodies That Inhibit Cell Motility and Tumor Cell Metastasis*", Biochemistry 1991, 30, pp. 3328–3334.

Taeko Dohi, Gustavo Nores, and Sen–itiroh Hakomori, "*An IgG$_3$ Monoclonal Antibody Established after Immunization with G$_{M3}$ Lactone: Immunochemical Specificity and Inhibition of Melanoma Cell Growth in Vitro and Vivo*", Cancer Research 48, pp. 5680–5685, Oct. 15, 1988.

Frontiers in Biotechnology, "*Biotech Gets a Grip on Cell Adhesion*", Science, pp. 906–908 vol. 260, May 14, 1993.

Drug Development, "*Going Back to the Future With Small Synthetic Compounds*", Science, pp. 910–913, vol. 260, May 14, 1993.

Stu Borman, "*Glycotechnology Drugs Begin to Emerge from the Lab*", C&EN, pp. 27–34 Jun. 28, 1993.

SYNTHETIC GLYCOAMINES THAT PROMOTE OR INHIBIT CELL ADHESION

FIELD OF THE INVENTION

The present invention relates to pharmaceuticals that affect cell adhesion, and more particularly, to a class of compounds that can inhibit or promote cell adhesion both in vitro and in vivo.

BACKGROUND OF THE INVENTION

Cell adhesion is one important property that differentiates multi-cellular organisms from simpler organisms such as bacteria. Cell adhesion is essential to the organization of higher organisms. Without cell adhesion, the organization of cells into tissues and tissues into organs would clearly be impossible. Likewise, the functioning of the immune system is also dependent on cell adhesion. Just as normal cell adhesion is essential to the normal functioning of higher organisms, abnormal cell adhesion is associated with a number of disease states such as intimation and cancer.

One manner in which cancer cells differ from normal tissue is in their cell adhesion and aggregation properties. Cell adhesiveness is one of the key cell surface-mediated properties that is altered during malignant transformation leading to metastatic dissemination of cancer cells. Metastasis is one of the most important malignant features of human cancer and represents the morphological stage of the generalization of the disease through the body of the tumor host. The abnormal adhesiveness of tumor cells is thought to contribute to the metastatic behavior of these cells. Implicit in the concept of metastasis is the separation of individual cells or small groups of cells from the primary tumor. It has been suggested that the intrinsically low adhesiveness of cancer cells contributes to separation. In particular, tumor cells have been shown to be more easily separated from solid tumors than are normal cells from corresponding tissues. Tumor cells have also been shown to be less adherent than normal cells to artificial substrates.

While the low adhesiveness of tumor cells contributes to the separation of cells from the primary tumor, metastasis is aided by the cells having some minimum degree of adhesion. The homotypic and heterotypic aggregation properties of tumor cells represent important biological features of malignancy because these properties of transformed cells contribute to the metastatic ability of neoplastic tumors. The concentration and size distribution of tumor cell clumps that enter the circulation play a significant role in the metastatic process. For example, intravenous injected tumor cells in clump form have a greater tendency to form metastases than do the same number of single tumor cells. Adhesion of cancer cells to other cells in circulatory system is required for the cancer cells to escape from the circulation system. Cancer cells that remain in the circulation system are known to have a very short lifetime. Hence, blocking of the homotypic and heterotypic adhesion of cancer cells can prevent escape of metastatic cells from the blood into the tissues and may cause a dramatic reduction or even complete prevention of metastasis.

The process of cell-cell recognition, association and aggregation consists of multiple steps, and a number of models of such a multistep process have been proposed. Generally the initial step is specific recognition between two cells in which multivalent homo-and heterotypic carbohydrate mediated interactions play a major role. Initial cell recognition through carbohydrate-carbohydrate or carbohydrate-protein (selectin) interaction is followed by protein-protein type adhesion, primarily mediated by $Ca^{++}$-sensitive adhesion molecules such as cadherins, or by proteins of immunoglobulin superfamily, or by pericellular adhesive meshwork proteins consisting of fibronectin, laminin, and their receptor systems (integrin). The third step of cell adhesion is the establishment of intercellular junctions, e.g., "adherent junctions and "gap junctions," in which a cell-cell communication channel is opened through specific structural proteins, and specialized cellular contacts such as tight junctions and desmosomes are formed.

Structural determinants participating in the homotypic and heterotypic aggregation of histogenetically different types of cells may be the carbohydrate determinants of the blood-group antigen (BGA) related glycoantigens. Recently, the experimental evidences have been generalized that support the concept that some of the BGA-related glycodeterminants which have been identified earlier as tumor associated carbohydrate antigens (TACA) function as key adhesion molecules. The recent studies have shown that cell adhesion through carbohydrate-carbohydrate or carbohydrate-selectin interactions occur at early initial stage of "cascade" multistep cell adhesion mechanism, and this reaction is prerequisite for subsequent cell adhesion directed by integrin or immunoglobulin based adhesion. Usually cells co-express on their surface the multiple components involved in "cascade" cell adhesion mechanism, and thus, this multistep adhesion reaction could be triggered by initial carbohydrate—carbohydrate or carbohydrate-selectin interaction. Evidence has been presented that specific glycosphingolipid-glycosphingolipid interaction initiates cell-cell adhesion, and may cooperate synergistically with other cell adhesion systems such as those involving integrins.

Thus, the key features of cancer cells adhesion are the preservation of cell recognition function and the initial reversible steps of cell-cell or cell substrate adhesion and the impairment of the ability to display secondary stable attachment, strong adhesion, and terminal tissue specific cell-cell and cell-substrate contacts. The profound defects in protein adhesive systems primarily mediated by cadherin and integrin families of adhesion receptor is characteristic of malignant transformation and may contribute significantly to the abnormal locomotion, motility, invasion and metastasis of cancer cells. However, the acquisition of certain adhesive properties by malignant cells is extremely important for invasion, motility and metastasis. Typically, metastatic cancer cells lose the adhesive characteristics of their parent coherent tissues, but acquire adhesive properties similar to those of embryo and/or circulating normal cells (e.g. leukocytes and platelets).

Aberrant glycosylation of cell-membrane macromolecules is one of the universal phenotypic attributes of malignant tumors. A rather limited number of molecular probes based on monoclonal anticarbohydrate antibodies now enables the detection of over 90% of the most widespread human forms of cancer. One of the most important biological consequences of aberrant glycosylation is the expression of cell adhesion determinants on the surface of cancer cells. The most characteristic manifestation of aberrant glycosylation of cancer cells is neo-synthesis (or ectopic synthesis), the synthesis of incompatible antigens and incomplete synthesis (with or without the accumulation of precursors) of the BGA-related glycoepitopes. BGA-related glycoepitopes are directly involved in the homotypic (tumor cells, embryonal cells) and heterotypic (tumor cells-normal cells) formation of cellular aggregates (e.g., Lewis X antigens; H-antigens, polylactosamine sequences; and T-and Tnantigens), which was demonstrated in different experimental systems. BGA-related alterations in the tissue glycosylation pattern are detected in benign (premalignant) tumors with risk of malignant transformation, in primary malignant tumors, and in metastases. Hence, they have been demonstrated as typical alterations in different stages of tumor progression. Therefore, the aberrant glycosylation in cancer is characterized by expression on the cell surface of tumor cells of certain BGA-related glycodeterminants. These changes were demonstrated as typical for different stages of tumor progression, including metastasis. The BGA-related glycodeterminants that are expressed on the surface of cancer cells function as cell adhesion molecules. They are present in cancer blood serum in biologically active form and may either stimulate or inhibit cell-cell interactions. The important fact is that in serum of all normal individuals circulate the naturally occurring anticarbohydrate antibodies of the same specificity.

The passage of metastatic cancer cells through blood and/or lymph compartment of host's body is one of the critical steps in metastatic dissemination of solid malignant neoplasms. Cancer cells that do not complete the transition quickly have exceedingly low survival rates in the circulatory system. There is a rapid phase of postintravasation (intramicrovascular) cancer cell death which is completed in less than 5 minutes and accounts for 85% of arrested cancer cells; this is followed by a slow phase of cell death, which accounts for the vast majority of the remainder. Mechanical trauma, which is a consequence of a shape transitions that occur when cancer cells enter and move along capillaries, has been considered as a most important factor contributing to the rapid death of the majority of cancer cells arrested in microvasculature of a different organs during metastatic dissemination.

Hence, inhibition of extravasation of cancer cells, blocking of their homotypic and heterotypic adhesion can prevent escape of metastatic cells from leaving the blood and entering the tissues. These considerations, as well as the analysis of cancer-related aberrations of cell adhesion mechanisms, suggest that agents that block cell adhesion may be of use in blocking metastasis. This therapy has been suggested as an additional complementary intervention for the current cancer treatment protocol, particularly designed to follow the surgical removal of a primary tumor.

The process of cell adhesion is also essential in the normal migration of cells. For example, in the healing of a wound, cells must migrate into the opening in the tissues in order to repair the opening. This cellular movement involves various classes of cells that move over the tissues surrounding the wound to reach the opening. Cellular adhesion is known to play a critical role in this type of cellular movement. Hence, compounds that enhance cellular adhesion are expected to enhance processes such as the healing of wounds. Similarly, the immune system both when functioning properly and in autoimmune diseases involves specific cellular adhesive reactions.

While potentially therapeutic compounds that affect cell adhesion are known, these compounds tend to be large macromolecules such as antibodies or peptides having carbohydrate moieties attached thereto. Maintaining such large structures in the circulatory system and/or targeting them to specific tissues presents a number of well known problems. In addition, the cost of manufacturing such compounds is quite high.

Broadly, it is the object of the present invention to provide an improved class of compounds that inhibit or enhance cell adhesion.

It is a further object of the present invention to provide cell adhesion affectors that consist of small molecular weight compounds.

It is a still further object of the present invention to provide cell adhesion affectors that may be synthesized using conventional chemical techniques.

It is yet another object of the present invention to provide cancer cell adhesion inhibitors that may be applied as antimetastatic agents.

These and other objects of the present invention will become apparent to those skilled in the art from the following detailed description of the invention and the accompanying drawings.

SUMMARY OF THE INVENTION

The present invention consists of a class of molecules that alter cell adhesion. A cell adhesion affector according to the present invention essentially consists of an amino acid linked to a carbohydrate wherein the amino acid and the carbohydrate are linked to form a compound chosen from the group consisting of Schiff bases, N-glycosides, esters, and Amadori products. The carbohydrate is preferably a monosaccharide or a small oligosaccharide. The carbohydrate and amino acid sub-units may be chemically modified. For example, the amino acid may be modified by covalently bonding other groups to the amino group, carboxyl group, or side chain group of the amino acid. The carbohydrate sub-unit is preferably a pentose such as arabinose, xylose, ribose, ribulose, a hexose such as fructose, deoxyfructose, galactose, glucose, mannose, tagatose, rhamnose, or a disaccharide based on two of the above such as maltose, lactose, maltulose, or lactulose.

DETAILED DESCRIPTION OF THE INVENTION

Figure 1:
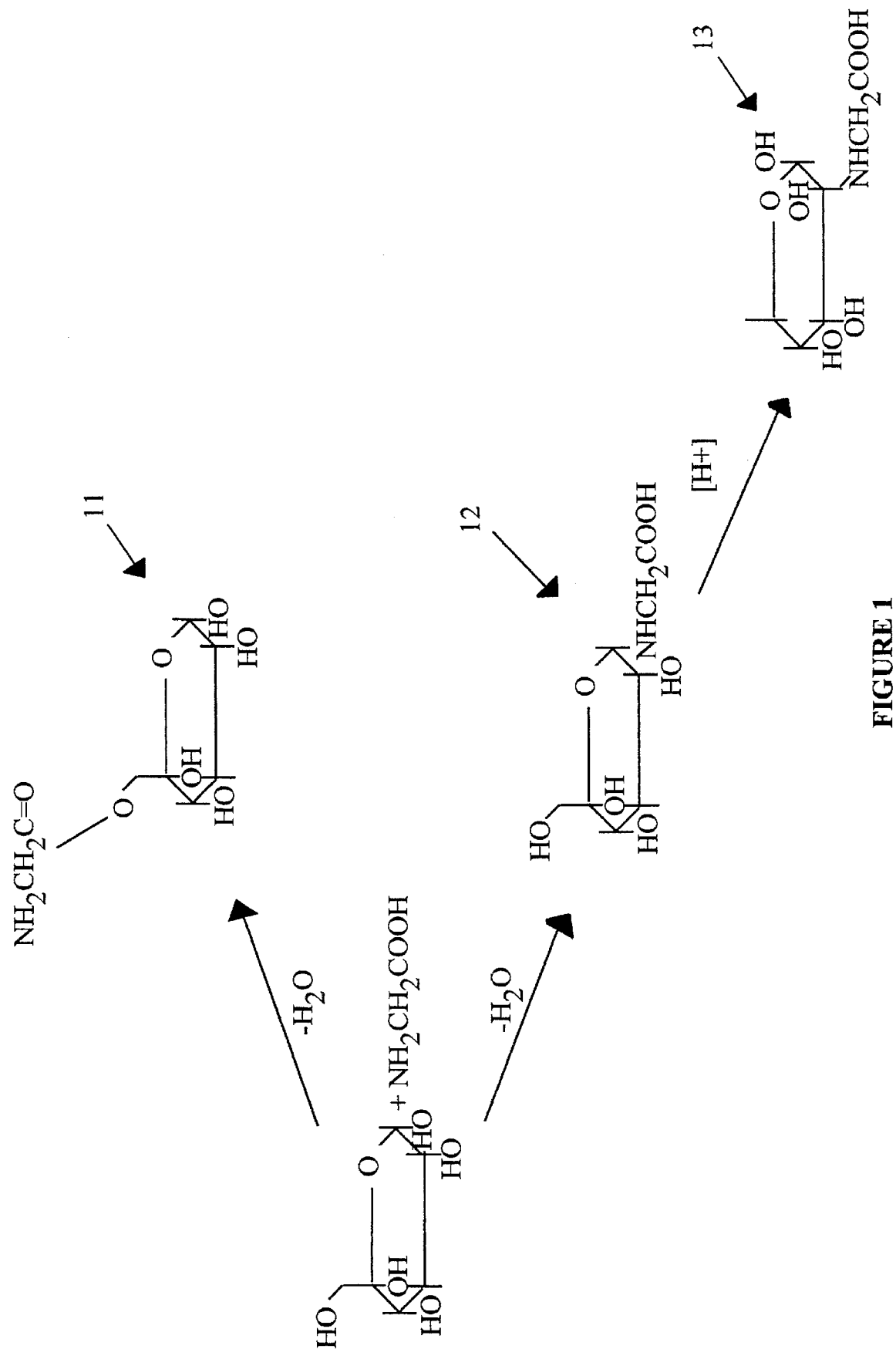
FIG. 1 illustrates the three types of compounds obtained from condensation reactions between glycine and glucose.

The present invention comprises a class of compounds that either enhance or inhibit cellular adhesion, depending on the particular compound chosen and the target cell type. The simplest molecules in the class may be viewed as having two sub-units. The first sub-unit is an amino acid, and the second sub-unit is a carbohydrate. The amino acid may be joined to the carbohydrate by any condensation of the carbohydrate and the amino acid. For example, esters, Schiff bases, and Amadori compounds may be used. Here, the aldehyde group and/or one or more of the hydroxyl groups of the carbohydrate are substituted by the corresponding covalent bonding with the amino acid. As will become clear from the following discussion, compounds according to the present invention may be synthesized and purified via conventional organic chemical procedures; hence, the compounds of the present invention may be obtained at far less cost than other potential affectors of cell adhesion that require complex chemistry and/or fermentation to provide the chemicals or their precursors.

Refer now to FIG. 1 which illustrates the chemical reactions for the compounds according to the present invention that utilize the amino acid glycine and the sugar glucose. The condensation of a carboxyl group of an amino acid, namely glycine, with a hydroxyl group of carbohydrate, namely glucose, leads to the formation of an ester bond affording glycosyl amino acidate which is shown at 11. The amino acid-aldose condensation with the involvement of the amino and aldehyde groups occurs much more readily and may lead to the formation of Schiff bases (open chain of carbohydrate), or N-glycosides(12) (cyclic form of carbohydrate) with subsequent development of Amadori compound(13). It will be apparent to those skilled in the art that the glycine can be replaced by any amino acid in the scheme shown in FIG. 1, and the glucose can be replaced by any sugar.

Preparation of Amadori Compounds

The most stable class of condensation product of an amino acid and a carbohydrate is an Amadori compound. The Amadori compounds are the preferred compounds because of their high biological activity, stability, relative simplicity of synthesis, isolation and purification in large quantities. The synthesis of Amadori compounds may be carried out as follows: A suspension of 0.2 mol of sugar (e.g., anhydrous D-glucose, D-galactose or D-lactose monohydrate, etc.), 2.0 g sodium bisulfite in 60 mL of methanol and 30 mL of glycerol is refluxed for 30 min., followed by the addition of 0.05–0.09 mol of amino acid and 8 mL of acetic acid. This solution is refluxed until about 80% of the amino acid is reacted, as evidenced by TLC. The resulting brown, syrupy solution is diluted with 1 volume of water, placed on a 2 cm by 30 cm column of Amberlite IRN-77 ion exchange resin (hydrogen form) pretreated with 8 mL of pyridine. The column is eluted with water, followed by 0.2N ammonium hydroxide or, if necessary, by a buffer that was 0.2M in pyridine and 0.4M in acetic acid. Fractions of approximately 25 mL are collected. Early fractions contain D-glucose, uncharged pigments and D-glucose-derived degradation products. The Amadori compound usually elute next and are collected until the concentration becomes too low. The combined fractions, which contain Amadori compound, are evaporated to 100 mL in vacuo, decolorized with charcoal (2.0 g) and evaporated in vacuo at 30° C. to syrups.

Some of the Amadori compound, along with unreacted amino acid elute near the end of the water wash and at the beginning of the ammonium hydroxide wash. The combined fractions, which contain Amadori compound, are evaporated to 100 mL in vacuo and decolorized with charcoal (2.0 g). This solution is placed on a second 2 cm by 30 cm column of Amberlite IRN-77 (pyridinium form, pretreated with 10 mL of acetic acid). The column is eluted with water and 25 mL fractions collected. The Amadori compounds usually elute immediately. Fractions containing the desired products are evaporated in vacuo at 30° C. to syrups.

In the preferred embodiment of the present invention, the reaction conditions as well as separation and purification methodology of Amadori products may be optimized as follows: Methanol-glycerol mixture(s) as solvent provides the optimal reaction temperature (80° C.) at refluxing, necessary solubility for carbohydrates find amino acids, and dehydration conditions to shift the equilibrium toward the N-glycosides. Small amounts of acetic acid and sodium pyrosulfite are necessary to create optimal acidity of the reaction mixtures (pH ca. 5.0) to catalyze the Amadori rearrangement which competes with acid hydrolysis to the starting reagents and to optimize the reducing conditions (eliminating $SO_2$) to prevent oxidative browning of Amadori products. These conditions lead to over 90% conversion of starting amino acids if a 3–4 fold molar excess of carbohydrate is employed. The progress of the reaction may be readily monitored by TLC analysis using ninhydrin as the spray reagent.

The method of isolation of Amadori product from reaction mixture containing Amadori product, amino acid, sugars, and browning products is based on application of ion-exchange chromatography. The reaction mixture is diluted by water and then loaded on a cationite column in H± or pyH± form (for acid labile Amadori products). Amino acids, Amadori product and charged browning products are retained on ion-exchange resin, and noncharged compounds (solvent, sugar and majority of browning products) are eluted by water. The next elutents usually are the aqueous pyridine, acetic acid, ammonia and their mixture depending on individual properties of corresponding Amadori product and amino acid. The pH range is chosen to provide separation of Amadori product and amino acid on the column due to difference in their acid-base properties. The portion of eluate containing pure Amadori product is evaporated and residue crystallized from convenient solvent or mixture. In practice, pure final Amadori product (95% or more) with yield range of 10–40% from corresponding amino acid is obtained. The chromatographic and structural characterization of synthetic products may be performed using TLC, reversed, ion-exchange and normal-phase HPLC, FAB-MS, elemental analysis, NMR, amino acid and carbohydrate analysis, and pH-potentiometric analysis, optical rotation, X-ray analysis.

Preparation of Schiff Base Compounds

The sodium salts of the Schiff bases, compounds SSGA-22 through 30 (See Table I below), may be prepared by the following procedure. The appropriate amino acid (10 mmol) is added to a solution of 0.23 g (10 mmol) of metallic sodium in 80 mL of anhydrous methanol, and the suspension is then refluxed until all solid is dissolved. To the resulting solution, 10 mmol of carbohydrate is added and this mixture is stirred at 25° to 40° C. under inert atmosphere until the solution is clear. Dry diethyl ether (usually 200–400 mL) is then poured carefully into the reaction mixture under vigorous stirring to precipitate desired product as amorphous or microcrystalline mass. The product is separated with filtration, washed with ether and dried over $CaCl_2$ in vacuo.

Preparation of Ester Compounds

The synthesis of compounds SSGA-20, 21, 37, and 38 (See Table I below) as their hydrochlorides utilizes the following procedure: A solution of 5 mmol of Boc-amino acid, imidazole (1.02 g, 15 mmol) and anhydrous sugar (1.80 g, 10 mmol) in 60 mL of dry pyridine is prepared and cooled to 0° C. Dicyclohexylcarbodiimide (DCC, 1.03 g, 5 mmol) is then added and the reaction mixture is stirred in an ice bath for 4 hours and at room temperature for an additional 12 hours. A precipitate of dicyclohexylurea is filtered off and the filtrate is evaporated in vacuo. The residue is partitioned between ethyl acetate (40 mL) and cold 10% citric acid in water (40 mL). The organic layer is washed with water, dried over $Na_2SO_4$ and evaporated in vacuo. The residue is crystallized from chloroform or methanol-chloroform, yielding the protected ester with 40–70% yield. This is dissolved in 15 mL of 1N solution of HCl in methanol or acetic acid and stirred at room temperature for an hour followed by addition of dry diethyl ether. The precipitate is collected by filtration and recrystallized from diethyl ether-THF.

The procedure for the synthesis of compounds SSGA-52 through 55 as their hydrochlorides utilizes the following procedure: To a solution of 5 mmol of Boc-amino acid and methyl α-D-glucopyranoside (1.94 g, 10 mmol) in 60 mL of dry acetonitrile a DCC (1.03 g, 5 mmol) is added at −1 0° C. The reaction mixture is stirred at 0° C. for 5 h and then overnight at room temperature. The protected ester is then isolated as described above with reference to SSGA-20, etc.

Modifications of the Basic Structure

In addition to the simple compounds consisting of an amino acid linked to a sugar, active compounds which are modifications of the basic structure have also been identified. These modifications may be separated into four classes. The first class involves the substitution of a small polypeptide for the amino acid. The second group involves substituting a polysaccharide for the sugar. The third class involves optical isomerization of an amino acid or modifications to the amino group, carboxyl group, hydrocarbon chains, or side chain group of the amino acids by covalently bonding other groups to one or more of these groups. Compounds SSGA-8, SSGA-13, SSGA-45, SSGA-10 and SSGA-39 belong to this class. Finally, one or more hydroxyl groups of the carbohydrate may be modified. For example, the hydroxyl group of the compounds based on D-glucose may be modified methylated to form compounds such as methyl α-D-glucopyranoside. Compounds SSGA-52 through SSGA-54 belong to this fourth class. For the purposes of the following discussion, the simplest class of molecules consisting of an amino acid coupled to a sugar will be referred to as the basic class.

Exemplary Compounds

Fifty-five members of the basic class or modifications thereof have been synthesized and all of these can be shown to affect cell adhesion in one or more cell adhesion assays. A summary of the chemical compounds investigated to date is given in Table I, below. The corresponding amino acid, method of linkage, and carbohydrate for a compound may be deduced from the compound's name. The full chemical name of each of the compounds listed in Table I may be found in Table II, below. Compounds SSGA-1 through SSGA-19, SSGA-31 through SSGA-36, and SSGA-39 through 51 are Amadori compounds. Compounds SSGA-22 through 30 are Schiff bases. Compounds SSGA-20, SSGA-21, SSGA-37, SSGA-38, and SSGA-52 through SSGA-55 are glycosyl esters of amino acids.

Some of the members of this group promote cell adhesion and some inhibit cell adhesion. In addition, some members promote cell adhesion in one cell type and inhibit cell adhesion in other cell types. The specific effect produced depends on the type of amino acid, sugar, coupling bond and the target cell type.

TABLE 1

| | Names of Synthetic Glycoamine Structural Analog |
|---|---|
| SSGA-1 | N-(1-Deoxy-D-fructos-1-yl)-β-alanine |
| SSGA-2 | N-(1-Deoxy-D-fructos-1-yl)-glycine |
| SSGA-3 | N-(1-Deoxy-D-fructos-1-yl)-L-phenylalanine |
| SSGA-4 | N-(1-Deoxy-D-fructos-1-yl)-L-tyrosine |
| SSGA-5 | N-(1-Deoxy-D-fructos-1-yl)-L-isoleucine |
| SSGA-6 | N-(1-Deoxy-D-fructos-1-yl)-L-aspartic acid |
| SSGA-7 | N-(1-Deoxy-D-fructos-1-yl)-L-glutamic acid |
| SSGA-8 | N-ε-(1-Deoxy-D-fructos-1-yl)-N-α-formyl-L-lysine |
| SSGA-9 | N-(1-Deoxy-D-fructos-1-yl)-γ-aminobutyric acid |
| SSGA-10 | N-(1-Deoxy-D-fructos-1-yl)-ε-aminocaproic acid |
| SSGA-11 | N-(1-Deoxy-D-fructos-1-yl)-L-tryptophan |
| SSGA-12 | N-(1-Deoxy-D-fructos-1-yl)-L-leucine |
| SSGA-13 | N-(1-Deoxy-D-fructos-1-yl)-D-leucine |
| SSGA-14 | N-(1-Deoxy-D-fructos-1-yl)-L-alanine |
| SSGA-15 | N-(1-Deoxy-D-fructos-1-yl)-L-valine |
| SSGA-16 | N-(1-Deoxy-D-fructos-1-yl)-L-proline |
| SSGA-17 | N-(1-Deoxy-D-tagatos-1-yl)-L-leucine |
| SSGA-18 | N-(1-Deoxy-D-maltulos-1-yl)-L-leucine |
| SSGA-19 | N-(1-Deoxy-D-lactulos-1-yl)-L-leucine |
| SSGA-20 | 6-O-(L-Prolyl)-D-glucose |
| SSGA-21 | 6-O-(L-Phenylalanyl)-D-glucose |
| SSGA-22 | N-(1-Deoxy-D-glucos-1-yl)-L-proline Na-salt |
| SSGA-23 | N-(1-Deoxy-D-glucos-1-yl)-L-phenylalanine Na-salt |
| SSGA-24 | N-(1-Deoxy-L-rhamnos-1-yl)-L-alanine Na-salt |
| SSGA-25 | N-(1-Deoxy-D-galactos-1-yl)-L-alanine Na-salt |
| SSGA-26 | N-(1-Deoxy-D-glucos-1-yl)-L-alanine Na-salt |
| SSGA-27 | N-(1-Deoxy-D-mannos-1-yl)-L-alanine Na-salt |
| SSGA-28 | N-(1-Deoxy-L--arabinos-1-yl)-L-alanine Na-salt |
| SSGA-29 | N-(1-Deoxy-D-maltos-1-yl)-L-alanine Na-salt |
| SSGA-30 | N-(1-Deoxy-D-xylos-1-yl)-L-alanine Na-salt |
| SSGA-31 | N-(1-Deoxy-D-ribulos-1-yl)-L-phenylalanine |
| SSGA-32 | N-(1-Deoxy-D-fructos-1-yl)-L-threonine |
| SSGA-33 | N-(1-Deoxy-D-maltulos-1-yl)-L-phenylalanine |
| SSGA-34 | N-(1,6-Dideoxy-L-fructos-1-yl)-L-proline |
| SSGA-35 | N-(1-Deoxy-D-tagatos-1-yl)-L-phenylalanine |
| SSGA-36 | N-(1-Deoxy-D-lactulos-1-yl)-L-phenylalanine |
| SSGA-37 | 6-O-(L-Valyl)-D-mannose |
| SSGA-38 | 6-O-(L-Prolyl)-D-galactose |
| SSGA-39 | N-(1-Deoxy-D-fructos-1-yl)-δ-aminovaleric acid |
| SSGA-40 | N-(1-Deoxy-D-fructos-1-yl)-L-serine |
| SSGA-41 | N-(1-Deoxy-D-lactulos-1-yl)-L-proline |
| SSGA-42 | N-(1-Deoxy-D-lactulos-1-yl)-L-valine |
| SSGA-43 | N-(1-Deoxy-D-fructos-1-yl)-L-methionine |
| SSGA-44 | N,N'-Di (1-deoxy-D-fructos-1-yl)-L-lysine |

TABLE 1-continued

Names of Synthetic Glycoamine Structural Analog

| | |
|---|---|
| SSGA-45 | N-α-(1-Deoxy-D-fructos-1-yl)-N-ε-formyl-L-lysine |
| SSGA-46 | N-α-(1-Deoxy-D-fructos-1-yl)-L-asparagine |
| SSGA-47 | N-(1-Deoxy-D-fructos-1-yl)-L-hydroxyproline |
| SSGA-48 | N-(1-Deoxy-D-tagatos-1-yl)-L-proline |
| SSGA-49 | N-(1-Deoxy-D-tagatos-1-yl)-L-valine |
| SSGA-50 | N'-α-(1-Deoxy-D-fructos-1-yl)-L-histidine |
| SSGA-51 | N,N-Di(1-deoxy-D-fructos-1-yl)-glycine |
| SSGA-52 | Methyl 6-O-(glycyl)-α-D-glucopyranoside |
| SSGA-53 | Methyl 2,3,4-tri-O-(glycyl)-6-O-(L-alanyl)-α-D-glucopyranoside |
| SSGA-54 | Methyl 6-O-(L-alanyl)-α-D-glucopyranoside |
| SSGA-55 | Methyl 2,3,-di-O-(L-alanyl)-α-D-glucopyranoside |

TABLE II

Full systematic names of synthetic glycoamine structural analogs.

| | |
|---|---|
| SSGA-1 | N-(1-Deoxy-D-arabino-hexulos-1-yl)-3-aminopropanoic acid |
| SSGA-2 | N-(1-Deoxy-D-arabino-hexulos-1-yl)-aminoetanoic acid |
| SSGA-3 | N-(1-Deoxy-D-arabino-hexulos-1-yl)-(S)-2-amino-3-phenylpropanoic acid |
| SSGA-4 | N-(1-Deoxy-D-arabino-hexulos-1-yl)-(S)-2-amino-3-(4-hydroxyphenyl)-propanoic acid |
| SSGA-5 | N-(1-Deoxy-D-arabino-hexulos-1-yl)-(2S,3S)-2-amino-3-methylpentanoic acid |
| SSGA-6 | N-(1-Deoxy-D-arabino-hexulos-1-yl)-(S)-2-aminobutane-1,4-dioic acid |
| SSGA-7 | N-(1-Deoxy-D-arabino-hexulos-1-yl)-(S)-2-aminopentane-1,5-dioic acid |
| SSGA-8 | (S)-6-(1-Deoxy-D-arabino-hexulos-1-amino)-2-N-formylaminohexanoic acid |
| SSGA-9 | N-(1-Deoxy-D-arabino-hexulos-1-yl)-4-aminobutanoic acid |
| SSGA-10 | N-(1-Deoxy-D-arabino-hexulos-1-yl)-6-aminohexanoic acid |
| SSGA-11 | (S)-2-(1-Deoxy-D-arabino-hexulos-1-amino)-3-(indol-3-yl)-propanoic acid |
| SSGA-12 | N-(1-Deoxy-D-arabino-hexulos-1-yl)-(S)-2-amino-4-methylpentanoic acid |
| SSGA-13 | N-(1-Deoxy-D-arabino-hexulos-1-yl)-(R)-2-amino-4-methylpentanoic acid |
| SSGA-14 | N-(1-Deoxy-D-arabino-hexulos-1-yl)-(S)-2-aminopropanoic acid |
| SSGA-15 | N-(1-Deoxy-D-arabino-hexulos-1-yl)-(S)-2-amino-3-methylbutanoic acid |
| SSGA-16 | (S)-1-(1-Deoxy-D-arabino-hexulos-1-yl)-2-pyrrolidine carboxylic acid |
| SSGA-17 | N-(1-Deoxy-D-lyxo-hexulos-1-yl)-(S)-2-amino-4-methylpentanoic acid |
| SSGA-18 | N-(1-Deoxy-4-O-(α-D-glucopyranos-1-yl)-D-arabino-hexulos-1-yl)-(S)-2-amino-4-methylpentanoic acid |
| SSGA-19 | N-(1-Deoxy-4-O-(β-D-galactopyranos-1-yl)-D-arabino-hexulos-1-yl)-(S)-2-amino-4-methylpentanoic acid |
| SSGA-20 | 6-O-((S)-2-pyrrolidine carboxyl)-D-glucose |
| SSGA-21 | 6-O-((S)-2-amino-3-phenylpropanoyl)-D-glucose |
| SSGA-22 | (S)-1-(1-Deoxy-D-glucos-1-yl)-2-pyrrolidine carboxylic acid |
| SSGA-23 | N-(1-Deoxy-D-glucos-1-yl)-(S)-2-amino-3-phenylpropanoic acid |
| SSGA-24 | N-(1,6-Dideoxy-L-mannos-1-yl)-(S)-2-aminopropanoic acid |
| SSGA-25 | N-(1-Deoxy-D-galactos-1-yl)-(S)-2-aminopropanoic acid |
| SSGA-26 | N-(1-Deoxy-D-glucos-1-yl)-(S)-2-aminopropanoic acid |
| SSGA-27 | N-(1-Deoxy-D-mannos-1-yl)-(S)-2-aminopropanoic acid |
| SSGA-28 | N-(1-Deoxy-L-arabinos-1-yl)-(S)-2-aminopropanoic acid |
| SSGA-29 | N-(1-Deoxy-4-O-(a-D-glucopyranos-1-yl)-D-glucos-1-yl)-(S)-2-aminopropanoic acid |
| SSGA-30 | N-(1-Deoxy-D-xylos-1-yl)-(S)-2-aminopropanoic acid |
| SSGA-31 | N-(1-Deoxy-D-erythro-pentulos-1-yl)-(S)-2-amino-3-phenylpropanoic acid |
| SSGA-32 | N-(1-Deoxy-D-arabino-hexulos-1-yl)-(2S,3R)-2-amino-3-hydroxybutanoic acid |
| SSGA-33 | N-(1-Deoxy-4-O-(α-D-glucopyranos-1-yl)-D-arabino-hexulos-1-yl)-(S)-2-amino-3-phenylpropanoic acid |
| SSGA-34 | (S)-1-(1,6-Dideoxy-L-arabino-hexulos-1-yl)-2-pyrrolidine carboxylic acid |
| SSGA-35 | N-(1-Deoxy-D-lyxo-hexulos-1-yl)-(S)-amino-3-phenylpropanoic acid |
| SSGA-36 | N-(1-Deoxy-4-O-(β-D-galactopyranos-1-yl)-D-arabino-hexulos-1-yl)-(S)-2-amino-3-phenylpropanoic acid |
| SSGA-37 | 6-O-((S)-2-amino-3-methylbutanoyl)-D-mannose |
| SSGA-38 | 6-O-((S)-2-pyrrolidine carboxyl)-D-galactose |
| SSGA-39 | N-(1-Deoxy-D-arabino-hexulos-1-yl)-5-aminopentanoic acid |
| SSGA-40 | N-(1-Deoxy-D-arabino-hexulos-1-yl)-(S)-2-amino-3-hydroxypropanoic acid |
| SSGA-41 | (S)-1-(1-Deoxy-4-O-(β-D-galactopyranos-1-yl)-D-arabino-hexulos-1-yl)-2-pyrrolidine carboxylic acid |
| SSGA-42 | N-(1-Deoxy-4-O-(β-D-galactopyranos-1-yl)-D-arabino-hexulos-1-yl)-(S)-2-amino-3-methylbutanoic acid |
| SSGA-43 | N-(1-Deoxy-D-arabino-hexulos-1-yl)-(S)-2-amino-4-methylthiobutanoic acid |

TABLE II-continued

Full systematic names of synthetic glycoamine structural analogs.

| | |
|---|---|
| SSGA-44 | N,N'-Di(1-deoxy-D-arabino-hexulos-1-yl)-(S)-2,6-diaminohexanoic acid |
| SSGA-45 | (S)-2-(1-Deoxy-D-arabino-hexulos-1-amino)-6-N-formylaminohexanoic acid |
| SSGA-46 | (S)-3-(1-Deoxy-D-arabino-hexulos-1-amino)-3-carboxypropanamide |
| SSGA-47 | (2S,4R)-1-(1-Deoxy-D-arabino-hexulos-1-yl)-4-hydroxy-2-pyrrolidine carboxylic acid |
| SSGA-48 | (S)-1-(1-Deoxy-D-lyxo-hexulos-1-yl)-2-pyrrolidine carboxylic acid |
| SSGA-49 | N-(1-Deoxy-D-lyxo-hexulos-1-yl)-(S)-2-amino-3-methylbutanoic acid |
| SSGA-50 | (S)-2-(1-Deoxy-D-arabino-hexulos-1-amino)-3-(1H-imidazol-4-yl)-propanoic acid |
| SSGA-51 | N,N-Di(1-deoxy-D-arabino-hexulos-1-yl)-aminoetanoic acid |
| SSGA-52 | Methyl 6-O-(2-aminoethanoyl)-α-D-glucopyranoside |
| SSGA-53 | Methyl 2,3,4-tri-O-(2-aminoethanoyl)-6-O-((S)-2-aminopropanoyl)-α-D-glucopyranoside |
| SSGA-54 | Methyl 6-O-((S)-2-aminopropanoyl)-α-D-glucopyranoside |
| SSGA-55 | Methyl 2,3-di-O-((S)-2-aminopropanoyl)-α-D-glucopyranoside |

Biological Activity

The compounds listed in Table I have been tested in one or more of a panel of 9 assays for their ability to promote or inhibit cell adhesion. The test results are summarized in Table III. The panel of tests can be divided into three classes of tests. In the first class of tests, (Tests 1–4 in Table III), the ability of a compound according to the present invention to inhibit or promote cell adhesion as measured by an in vitro Murine cancer assay was determined, this test will be referred to as the cell aggregation assay in the following discussion. Tumor cells were obtained from the indicated tumor tissue by standard trypsinization procedures. Then, $10^6$ cells were cultured at 37° C. in 5% $CO_2$ by using RPM1 1640 containing 10% fetal calf serum, 2 mM glutamine, and 1 mM pyruvate, 100 IU of penicillin per mL, 20 mg of gentamicin per mL, and 100 IU of streptomycin per mL (growth medium). The cells were cultured with and without a adhesion affector according to the present invention. The concentration range for the tested compounds was 20 μM to 15 mM. The cells were incubated for periods of 24–72 hours and 5 days in 0.4–1.0 mL (final volume) of growth medium in wells of a 96-well cell culture plate. The aggregates containing more than 4–5 cells (in suspension and substrate-attached) in each well were counted. Live cell counts were obtained by trypan blue dye exclusion.

The second class of assay (Tests 5–7 in Table III) involves the measurement of metastatic activity in vivo. The assay was carried out as follows: Cancer cells of the indicated type were incubated for 1 hour in 5% $CO_2$ at 37° C. in RPMI-1640 medium with and without addition of 1 mM (final concentration) of tested compounds. Subsequently $2.10^5$ melanoma or carcinoma cells were injected into tail vein of C57B1 2–3 month old male mice and 21 days later, the lung metastases were counted. Similarly, $0.25.10^6$ fibrosarcoma cells were injected into the tail vein of BALB/c 8–10 week old male mice and 21 days later, the lung metastases counted. All three general inhibitors of in vitro cancer cell aggregation showed a significant inhibition of in vivo experimental lung metastasis after intravenous inoculation of B16 melanoma cells. SSGA-12 and SSGA-13 have caused a 70% and 71% inhibition of lung colonization, respectively. Inhibition of B16 melanoma lung metastasis also showed that synthetic compound SSGA-19 was inhibitory with a 63% of inhibition of lung colonization. The 2 most effective synthetic inhibitors of in vitro melanoma cell aggregation also inhibited lung metastasis the most. SSGA-9 and SSGA-10 inhibited the lung colonization by melanoma cells at 79% and 87%, respectively. For comparison, SSGA-5 which is not an inhibitor of the B16 melanoma cell line in the in vitro aggregation test is only a weak inhibitor in vivo. SSGA-5 inhibited lung colonization only 35% in the above described assay.

The third class of assays (Tests 8–9 in Table III) will be referred to as the in vitro human cancer assay. The MDA-MB-435 human breast carcinoma cell line was isolated originally from pleural effusion of a patient with breast carcinoma and was found to be highly metastatic from the mammary fat pad (m.f.p.) tumors as well as after i.v. injection in nude mice.

The TXM-13 human melanoma cell line were originally isolated from brain metastases and were established from surgical specimens from melanoma patients at The University of Texas M.D. Anderson Cancer Center (Houston, Tex.). TXM-13 human melanoma cell line was found to be highly tumorigenic and metastatic in nude mice.

The metastatic and tumorigenic properties of human melanoma and breast carcinoma cell lines in nude mice were found to correspond well with their colony-forming efficiency in dense agarose. Hence, the tests were carried on agarose.

The tumor cells were maintained in tissue culture in minimum essential medium (MEM) supplemented with 5 or 10% fetal bovine serum (FBS), sodium pyruvate, nonessential amino acids, L-glutamine, and 2-fold vitamin solution (Gibco, Grand Island, N.Y.). The cultures were maintained on plastic and incubated in 5% $CO_2$-95% air at 37° C. in a humidified incubator. All cultures were free of Mycoplasma and the following murine viruses: reovirus type 3; pneumonia virus; K virus; Theiler's encephalitis virus; Sendai Virus; minute virus; mouse adenovirus; mouse hepatitis virus; lymphocytic choriomeningitis virus; ectromelia virus; lactate dehydrogenase virus (all assayed by MA Bioproducts, Walkersville, Md.).

The Agarose cultures used in the assays were prepared as follows: Agarose (Sigma Chemical Co. St. Louis, Mo.) was dissolved in distilled water and autoclaved at 120° C. for 20 min. MEM with 10% FBS and 0.6% agarose was plated in 30-mm-diameter plastic dishes to provide a base layer (1 mL per dish). Suspensions of breast carcinoma cells were filtered through 20 mm Nitex nylon mesh (Tetko, Elmsford, N.Y.) to remove any clumps of cells and then mixed with MEM containing 10% FBS (20% FBS for cultures of MDA-MB-361 cells) and different concentrations of agarose. This mixture was overlaid on the base layers. The cell number per dish in 1.5 mL was $5 \times 10^3$ for cultures of 0.3 and 0.6% agarose, $10^4$ cells in 0.9% agarose, and $2 \times 10^4$ cells in 1.2% agarose. The culture dishes were incubated at 37° C. in a humidified incubator in a 5% $CO_2$-95% air atmosphere. The numbers and diameters of tumor colonies examined 30 days after plating were determined using a microscope equipped with a Filar micrometer (Cambridge Instruments, Deer Lake, Ill.).

The MDA-MB-435 inhibition of colony formation in agarose assay was carded out as follows: Cells were incubated for 1 h at 37° C. in the presence of compound at 0.6 to 10 mM, then mixed with agarose to achieve a final concentration of 0.3 or 0.9% and plated in 35 mm wells. Colonies of diameter greater than 50 μm were counted at 14 days (0.3% agarose) of 21–25 days (0.9% agarose). Percent inhibition was calculated by comparison with colony numbers in control cultures (cells incubated with medium alone).

The TXM-13 inhibition of colony formation in agarose test was carried out as follows. TXM-13 human melanoma cells were plated in agarose following incubation for one hour with the compounds at 0.6 to 10 mM. The assays for activity of compounds #9 and #10 produced low colony numbers in control and test groups (inoculum of $5 \times 10^3$ per dish in 0.3% agarose and $10^4$ per dish in 0.9% agarose). Cell inoculum was increased (x 2) for the other experiments, producing larger colony numbers. Colony numbers were counted on day 21–25 after plating.

TABLE III

Summary of testing of the synthetic structural analogs of glycoamines.

| Compound number | Murine cancer, in vitro assay | | | | Murine cancer, in vivo assay | | | Human cancer, in vitro assay | |
|---|---|---|---|---|---|---|---|---|---|
| | 1 | 2 | 3 | 4 | 5 | 6 | 7 | 8 | 9 |
| SSGA-1  | ++ | ++ | —  | +  | ++ | ++ |    | ++ |    |
| SSGA-2  | ++ | +  | —  | 0  | 0  | ++ |    | ++ |    |
| SSGA-3  | ++ | ++ | —  | ++ | 0  | ++ |    | ++ | ++ |
| SSGA-4  | ++ | —  | —  |    | 0  |    |    |    |    |
| SSGA-5  | ++ | —  | —  | +  | 0  |    | 0  |    |    |
| SSGA-6  | ++ | —  | —  | 0  | 0  |    |    |    |    |
| SSGA-7  | 0  |    | ++ |    |    |    |    |    |    |
| SSGA-8  | 0  |    | ++ | +  | 0  |    |    |    |    |
| SSGA-9  | —  | —  | ++ | +  | 0  |    | ++ | 0  | 0  |
| SSGA-10 | —  | ++ | ++ | +  |    |    | ++ | ++ | 0  |
| SSGA-11 |    |    |    | ++ |    |    |    |    |    |
| SSGA-12 | +  | +  | +  | ++ |    | ++ | ++ | ++ | ++ |
| SSGA-13 | ++ | ++ | +  | ++ | ++ | ++ | ++ | ++ | ++ |
| SSGA-14 | ++ |    | —  | +  |    |    |    | +  | ++ |
| SSGA-15 | 0  |    | 0  | +  | 0  |    |    |    |    |
| SSGA-16 | ++ |    | 0  | 0  |    |    |    | ++ | ++ |
| SSGA-17 | ++ | —  | ++ |    |    | ++ |    |    |    |
| SSGA-18 | ++ | ++ |    |    | 0  |    |    |    |    |
| SSGA-19 | +  | ++ | +  | ++ |    | ++ | ++ | ++ | ++ |
| SSGA-20 | ++ |    | +  |    |    | ++ |    |    |    |
| SSGA-21 | ++ |    | 0  |    |    |    |    |    |    |
| SSGA-22 | ++ | 0  | —  |    |    |    |    |    |    |
| SSGA-23 | ++ | —  | —  |    |    |    |    |    |    |
| SSGA-24 | —  | —  | ++ |    |    |    |    |    |    |
| SSGA-25 | 0  | 0  | +  |    |    |    |    |    |    |
| SSGA-26 | —  | 0  | +  |    |    |    |    |    |    |
| SSGA-27 | —  | 0  | +  |    |    |    |    |    |    |
| SSGA-28 | 0  | 0  | +  |    |    |    |    |    |    |
| SSGA-29 | —  | 0  | +  |    |    |    |    |    |    |
| SSGA-30 | —  | 0  | ++ |    |    |    |    |    |    |
| SSGA-31 | 0  |    | ++ |    |    |    |    |    |    |
| SSGA-32 | 0  |    | +  |    |    |    |    |    |    |
| SSGA-33 | +  |    | ++ |    |    |    |    |    |    |
| SSGA-34 | —  |    | ++ |    |    |    |    |    |    |
| SSGA-35 | 0  | ++ | ++ |    |    |    |    |    |    |
| SSGA-36 | +  | ++ | +  |    |    | ++ |    |    |    |
| SSGA-37 | +  |    | —  |    |    |    |    |    |    |
| SSGA-38 | 0  |    | +  |    |    |    |    |    |    |
| SSGA-39 |    |    |    | —  |    |    |    |    |    |
| SSGA-40 |    |    |    | +  |    |    |    |    |    |
| SSGA-41 |    |    |    | +  |    |    |    |    |    |
| SSGA-42 |    |    |    | +  |    |    |    |    |    |
| SSGA-43 |    |    |    | +  |    |    |    |    |    |
| SSGA-44 |    |    |    | +  |    |    |    |    |    |
| SSGA-45 |    |    |    | +  |    |    |    |    |    |
| SSGA-46 |    |    |    | +  |    |    |    |    |    |
| SSGA-47 |    |    |    | +  |    |    |    |    |    |
| SSGA-48 |    |    |    | +  |    |    |    |    |    |
| SSGA-49 |    |    |    | +  |    |    |    |    |    |
| SSGA-50 |    |    |    | +  |    |    |    |    |    |
| SSGA-51 |    |    |    | +  |    |    |    |    |    |
| SSGA-52 | +  |    |    |    |    |    |    |    |    |

TABLE III-continued

Summary of testing of the synthetic structural analogs of glycoamines.

| Compound number | Murine cancer, in vitro assay | | | | Murine cancer, in vivo assay | | | Human cancer, in vitro assay | |
|---|---|---|---|---|---|---|---|---|---|
| | 1 | 2 | 3 | 4 | 5 | 6 | 7 | 8 | 9 |
| SSGA-53 | + | | | | | | | | |
| SSGA-54 | + | | | | | | | | |
| SSGA-55 | 0 | | | | | | | | |

Test Num.
1 MX-induced fibrosarcoma, in vitro cell aggregation assay;
2 3LL (Lewis) carcinoma, in vitro cell aggregation assay;
3 B16 melanoma, in vitro cell aggregation assay;
4 F10 B16 melanoma metastatic cell line, in vitro cell aggregation assay;
5 MX-induced fibrosarcoma, in vivo experimental metastasis assay;
6 3LL (Lewis) carcinoma, in vivo experimental metastasis assay;
7 B16 melanoma, in vivo experimental metastasis assay;
8 MDA-MB-435 human breast carcinoma metastatic cell line, in vitro colony formation in agarose assay;
9 TXM-13 human melanoma metastatic cell line, in vitro colony formation in agarose assay;
Result
+ Inhibition
++ Strong Inhibition (>50%)
− Stimulation
— Strong Stimulation (>50%)
0 No effect The results of the various assays are summarized in Table III. It should be noted that, with the exception of SSGA-55 which was only examined in one test, all of the compounds either promote or inhibit cell adhesion in at least one test. These data suggest that the class of compounds described in the present invention are all affectors of cell adhesion. Some compounds, such as SSGA-12, SSGA-13, SSGA-36 and SSGA-19 inhibit cell aggregation in every test in which they were examined suggesting that these compounds are "universal" inhibitors. Other compounds exhibit different effects depending on the cell type and assay suggesting that these compounds are cell type specific in their inhibition or promotion of cell adhesion.

Naturally Occurring Glycoamines

It should be noted that larger glycoamines that include an amino acid linked to a sugar by one of the above-described links have been isolated from the blood stream of patients with various cancers. These compounds have been investigated as physiological components of human and rodent blood serum that merit interest as potential tumor makers. The level of these substances is substantially increased in blood serum from humans and animals with different forms of malignant solid tumors and leukemias. Structurally the glycoamines detected in blood represent carbohydrate-amino acid conjugates containing from 5 to 29 amino acids and from 1 to 17 carbohydrate residues. The chemical structure of glycoamines reveal mono-, di- and trisaccharides bound to the amino acids and assembled into higher molecular weight compounds via the formation of ester, Schiff base and Amadori product-type bonds with the involvement of the amino groups of amino acids and hydroxyl, aldehyde or keto groups of the carbohydrates. The function of these naturally occurring glycoamines has yet to be determined.

While large glycoamines have been detected in nature, the much simpler compounds of the present invention have not been detected in blood. If the compounds of the present invention exist in blood, they are presumably at concentrations below the detection threshold which is approximately 1 μMolar.

Various modifications to the present invention will become apparent to those skilled in the art from the foregoing description and accompanying drawings. Accordingly, the present invention is to be limited solely by the scope of the following claims.

What is claimed is:

1. A method of inhibiting the adhesion of cells to one another, said method comprising the step of bringing said cells into contact with a compound comprising of a polypeptide having one or more amino acids, one of said amino acids being linked to a carbohydrate to form a compound chosen from the group consisting of Schiff bases, N-glycosides, esters, and Amadori products, said compound being present in sufficient concentration to inhibit the adhesion of said cells to one another.

2. The method of claim 1 wherein said carbohydrate is a monosaccharide.

3. The method of claim 1 wherein said carbohydrate is a disaccharide.

4. The method of claim 1 wherein said carbohydrate is chosen from the group consisting of arabinose, xylose, ribose, ribulose, fructose, deoxyfructose, galactose, rhamnose, glucose, mannose, tagatose, maltose, lactose, maltulose, and lactulose.

5. The method of claim 1 wherein a reactive group of said carbohydrate is covalently modified.

6. The method of claim 1 wherein a reactive group of one of said amino acids is covalently modified.

7. The method of claim 1 wherein said amino acid is an L-amino acid.

8. The method of claim 1 wherein said amino acid is a D-amino acid.

* * * * *